United States Patent [19]
Hermeling

[11] Patent Number: 5,326,438
[45] Date of Patent: Jul. 5, 1994

[54] PHTHALADEHYDE TETRAALKYL ACETALS, THE PREPARATION THEREOF AND THE USE THEREOF AS STORAGE COMPOUNDS

[75] Inventor: Dieter Hermeling, Frankenthal, Fed. Rep. of Germany

[73] Assignee: BASF Aktiengesellschaft, Ludwigshafen, Fed. Rep. of Germany

[21] Appl. No.: 38,084

[22] Filed: Mar. 29, 1993

Related U.S. Application Data

[62] Division of Ser. No. 907,976, Jul. 2, 1992, abandoned.

[30] Foreign Application Priority Data

Jul. 5, 1991 [DE] Fed. Rep. of Germany ....... 4122314

[51] Int. Cl.⁵ ................................................ C25B 3/02
[52] U.S. Cl. ..................................................... 204/78
[58] Field of Search ...................... 204/78; C25B 3/02

[56] References Cited

U.S. PATENT DOCUMENTS

| | | | |
|---|---|---|---|
| 4,318,787 | 3/1982 | Peterson | 204/147 |
| 4,588,482 | 5/1986 | Degner | 204/59 R |
| 5,208,384 | 5/1993 | Hermeling | 568/426 |

FOREIGN PATENT DOCUMENTS

| | | |
|---|---|---|
| 012240A2 | 6/1980 | European Pat. Off. . |
| 3108790A1 | 9/1982 | Fed. Rep. of Germany . |
| 3421976A1 | 12/1985 | Fed. Rep. of Germany . |

OTHER PUBLICATIONS

Journal Chem. Res. 1986, pp. 228–229, "Electrochemical Methoxylation of o-xylene: Isolation of Cyclohexa-1,4-dienes" by Fructuoso Barba et al.

*Primary Examiner*—Kathryn Gorgas
*Attorney, Agent, or Firm*—Keil & Weinkauf

[57] ABSTRACT

Phthalaldehyde tetraalkyl acetals are prepared by electrochemical oxidation of substituted xylenes and used as stable compounds for storing phthalaldehydes.

7 Claims, No Drawings

PHTHALADEHYDE TETRAALKYL ACETALS, THE PREPARATION THEREOF AND THE USE THEREOF AS STORAGE COMPOUNDS

CROSS-REFERENCE TO RELATED APPLICATION

This application is a divisional of application Ser. No. 07/907,976, filed on Jul. 2, 1992, now abandoned.

BACKGROUND OF THE INVENTION

1. Field of the Invention

The present invention relates to novel phthalaldehyde tetraalkyl acetals, to a process for preparing them by electrochemical oxidation, and to the use thereof as compounds for storing the corresponding aldehydes.

Acetals are not just of particular interest in protective group chemistry because they protect reactive aldehydes from unwanted reactions; they are also used as compounds which are stable to heat and oxidation for storing aldehydes which can be liberated quantitatively from the acetals as required under mild conditions.

Of particular interest are phthalaldehydes which are used, for example, as disclosed in DE 3 421 976 A1 as intermediates for the preparation of dyes, optical brighteners or specific polymers.

2. Description of the Prior Art

Phthalaldehyde tetraalkyl acetals can be prepared, for example as disclosed in DE 3 108 790 A1, by reacting α, α, α', α'-tetrahaloxylenes with alkali metal alcoholates. However, this process has the disadvantage that the tetrahaloxylenes are toxicologically unacceptable and can be obtained with only unsatisfactory selectivity.

According to DE 3 421 976 A1, phthalaldehyde tetraalkyl acetals can be prepared electrochemically by oxidation of the corresponding bis(alkoxymethyl)benzenes. However, since these starting materials are synthesized from bis(halomethyl)benzenes, the abovementioned problems arise in this case, too.

SUMMARY OF THE INVENTION

It is an object of the present invention to make phthalaldehyde tetraalkyl acetals available in a straightforward process without the need to use halogen-containing starting materials.

We have found that this object is achieved by electrochemical oxidation of substituted o-xylenes of the formula II

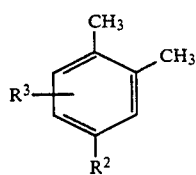

where $R^2$ is $C_3$-$C_{20}$-alkyl, $C_3$-$C_{20}$-cycloalkyl or $C_4$-$C_{20}$-alkyl-cycloalkyl and $R^3$ is hydrogen or $R^2$, in the presence of an alcohol $R^1OH$ where $R^1$ is $C_1$-$C_6$-alkyl, to phthalaldehyde tetraalkyl acetals of the formula I

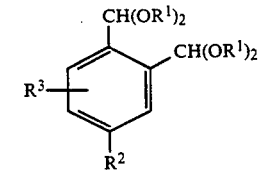

where $R^1$, $R^2$ and $R^3$ have the abovementioned meanings, so that environmentally friendly access to phthalaldehyde tetraalkyl acetals without halogen-containing precursors is now possible.

The present invention thus relates to phthalaldehyde tetraalkyl acetals of the formula I given above.

The electrochemical oxidation of substituted and unsubstituted xylenes results, according to EP 12 240 A2, in methylbenzaldehyde dialkyl acetals. According to J. Chem. Research (1986), 228–229, the acetals as described in the example of the electrolysis of o-xylene are converted in the subsequent oxidation step into the corresponding orthoesters, while the second methyl group remains unchanged.

In view of this, it was surprising that the substituted xylenes of the formula II can be electrochemically oxidized in good yields to give the phthalaldehyde tetraalkyl acetals of the formula I.

The present invention accordingly also relates to a process in which substituted xylenes of the formula II given above are electrochemically oxidized to phthalaldehyde tetraalkyl acetals.

DESCRIPTION OF THE PREFERRED EMBODIMENTS

Alcohols of the formula $R^1OH$ which are used are those with 1–6 carbons, preferably 1–4 carbons. Methanol and ethanol are particularly preferred.

It is preferable that the α-C atoms in the substituents $R^2$ and $R^3$ carry no hydrogen because the presence of hydrogen on the α-C atom results in by-products in the electrochemical oxidation and thus a reduction in the yields.

Suitable substituents $R^2$ are alkyls of 3–20, preferably 4–12 carbons, such as n-butyl, isobutyl, tert-butyl, n-pentyl, tert-amyl, 1-methylbutyl, 2,2-dimethylpropyl, n-hexyl, 1-methylpentyl, 1,1-dimethylbutyl, 1,1,2-trimethylpropyl, 1-ethyl-1-methylpropyl, 2,2n-heptyl, 1-methylhexyl, 1,1-dimethylpentyl, 1-ethyl-1-methylbutyl, 1,1-diethylpropyl, 1-methyl-1-propylpropyl, 1-ethyl-1-propylethyl, 1-methyl-1-butylethyl, 1,1,2,2-tetramethylpropyl, n-octyl, 1,1-dimethylhexyl, 1-ethyl-1-methylpentyl, 1,1-diethylbutyl, 1-methyl-1-propylbutyl, 1-ethyl-1-propylpropyl, 1,1,3,3-tetramethylbutyl, 1,1-dimethylheptyl, 1,1-dimethyloctyl, 1,1-dimethylnonyl, 1,1-dimethyldecyl, particularly preferably tert-butyl, tert-amyl, 1,1-dimethylbutyl, 1,1,2-trimethylpropyl, 1,1-dimethylpentyl and 1,1,2,2-tetramethylpropyl, cycloalkyl of 3–20, preferably 5–12, carbons, such as cyclopentyl, cyclohexyl, cycloheptyl, cyclooctyl, cyclononyl, cyclodecyl, cycloundecyl, cyclododecyl, particularly preferably cyclopentyl, cyclohexyl and cycloheptyl, or alkyl-cycloalkyl of 4–20, preferably 6–12, carbons, such as 1-methylcyclopentyl, 1-methylcyclohexyl, 1-ethylcyclohexyl, 1,4-dimethylcyclohexyl, 1,3-dimethylcyclohexyl, 1,3,5-trimethylcyclohexyl, 1-isopropylcyclohexyl, 1-tert-butylcyclohexyl, particularly preferably 1-methylcyclopentyl, 1-methylcyclohexyl and 1,3,5-trimethylcyclohexyl.

$R^3$ is hydrogen or $R^2$.

Preferred compounds according to the invention are:
4-tert-butyl-1,2-bis(dimethoxymethyl)benzene
4-tert-amyl-1,2-bis(dimethoxymethyl)benzene
4-(1,1-dimethylbutyl)-1,2-bis(dimethoxymethyl)benzene
4-(1,1,2-trimethylpropyl)-1,2-bis(dimethoxymethyl)benzene
4-(1,1-dimethylpentyl)-1,2-bis(dimethoxymethyl)benzene
4-(1,1,2,2-tetramethylpropyl)-1,2-bis(dimethoxymethyl)benzene
4-(1,1-dimethylhexyl)-1,2-bis(dimethoxymethyl)benzene
4-(1,1,3,3-tetramethylbutyl)-1,2-bis(dimethoxymethyl)benzene
4-(1,1-dimethylheptyl)-1,2-bis(dimethoxymethyl)benzene
4-(1,1-dimethyloctyl)-1,2-bis(dimethoxymethyl)benzene
4-(1-methylcyclopentyl)-1,2-bis(dimethoxymethyl)benzene
4-(1-methylcyclohexyl)-1,2-bis(dimethoxymethyl)benzene
4-(1,4-dimethylcyclohexyl)-1,2-bis(dimethoxymethyl)benzene
4-(1,3,5-trimethylcyclohexyl)-1,2-bis(dimethoxymethyl)benzene
4-tert-butyl-1,2-bis(diethoxymethyl)benzene
4-tert-amyl-1,2-bis(diethoxymethyl)benzene
4-(1,1-dimethylbutyl)-1,2-bis(diethoxymethyl)benzene
4-(1,1,2-trimethylpropyl)-1,2-bis(diethoxymethyl)benzene
4-(1,1-dimethylpentyl)-1,2-bis(diethoxymethyl)benzene
4-(1,1,2,2-tetramethylpropyl)-1,2-bis(diethoxymethyl)benzene
4-(1,1-dimethylhexyl)-1,2-bis(diethoxymethyl)benzene
4-(1,1,3,3-tetramethylbutyl)-1,2-bis(diethoxymethyl)benzene
4-(1,1-dimethylheptyl)-1,2-bis(diethoxymethyl)benzene
4-(1,1-dimethyloctyl)-1,2-bis(diethoxymethyl)benzene
4-(1-methylcyclopentyl)-1,2-bis(diethoxymethyl)benzene
4-(1-methylcyclohexyl)-1,2-bis(diethoxymethyl)benzene
4-(1,4-dimethylcyclohexyl)-1,2-bis(diethoxymethyl)benzene
4-(1,3,5-trimethylcyclohexyl)-1,2-bis(diethoxymethyl)benzene The compounds of the formula I are novel and can be prepared in an electrochemical process in electrolysis cells conventional in industry.

Undivided continuous flow cells are preferably used. Examples of suitable anodes are noble metal electrodes such as platinum or oxide electrodes such as $Ti/RuO_x$, $RuO_2$ or $Cr_2O_3$. Graphite is the preferred anode material. Examples of suitable cathodes are steel, iron, nickel, copper, zinc and carbon, as well as noble metals such as platinum. Graphite is the preferred cathode material. The electrolyte is composed of the starting compound of the formula II, of the alcohol $R^1OH$ and of an auxiliary electrolyte. Suitable auxiliary electrolytes are neutral salts, acids and bases. Examples of neutral salts are fluorides such as KF, sulfonates such as $NaSO_3Ph$, sulfates such as $(CH_3)_4NSO_4CH_3$, tetrafluoroborates such as $NaBF_4$, phosphates and phosphonates.

Examples of acids are sulfuric acid, alkyl- and arylsulfonic acids such as methyl- or benzenesulfonic acid. Examples of bases which are used are alcoholates such as $NaOCH_3$ or hydroxides such as KOH.

The electrolyte has the following composition, for example:
1 to 49, preferably 5-30, % by weight of compound of the formula II
50-98.9, preferably 70-95, % by weight of $R^1OH$
0.1-5, preferably 0.2-3, % by weight of auxiliary electrolyte.

The current density in the process according to the invention can be chosen within wide limits, for example 0.1-25 $A/dm^2$, preferably 1-10 $A/dm^2$. The temperatures can also be varied within wide limits. Thus, the oxidations can be carried out at 0°-100° C., preferably at 20°-80° C. The electrolysis temperature depends, inter alia, on the alcohol $R^1OH$. The process is carried out in every case above the boiling point of the alcohol $R^1OH$. The electrolyses are preferably carried out under atmospheric pressure, but can also be carried out under a superatmospheric pressure up to 10 bar. The resulting elevation in boiling point makes it possible, for example, also to electrolyze in methanol above 60° C.

The starting compounds of the formula II which cannot be bought can be prepared straightforwardly by alkylation of xylene in a conventional manner.

Very substantial conversion of the starting compounds of the formula II is possible. Unreacted precursor, and the intermediates occurring in the electrolysis, can be returned to the electrolysis. The electrolysis can be carried out both continuously and batchwise. The electrolysis discharges are worked up by conventional methods, preferably by distillation.

The phthalaldehyde tetraalkyl acetals according to the invention are suitable as stable compounds for storing the corresponding phthalaldehydes, because the acetals can be converted into the aldehydes in a conventional manner by hydrolysis (see, for example, Houben-Weyl, Meth. d. org. Chemie, 4th edition, Vol. 7/1, Oxygen compounds II, pages 423-428; G. Thieme Verlag, Stuttgart, 1954).

EXAMPLES

EXAMPLE 1

Electrosynthesis of
4-tert-butyl-1,2-bis(dimethoxymethyl)benzene

Apparatus: undivided cell with 11 bipolar electrodes.
Anodes: graphite.
Electrolyte: 450 g (2.778 mol) of 4-tert-butyl-1,2-dimethylbenzene, 30 g of sodium benzenesulfonate and 2520 g of methanol.
Cathodes: graphite.
Current density: 3.4 $A/dm^2$.
Electrolysis temperature: 46° C.
Electrolysis with 17 F/mol of 4-tert-butyl-1,2-dimethylbenzene.
The electrolyte is pumped at 200 l/h through the cell during the electrolysis.
Working up:
After the electrolysis is complete, methanol is removed by distillation under atmospheric pressure until the bottom temperature is 120° C., the conducting salt is removed by filtration and the filtrate is purified by distillation under reduced pressure. 467 g (1.656 mol) of 4-tert-butyl-1,2-bis(dimethoxymethyl)benzene are obtained.

Yield: 57%

$^{13}$C-NMR (CDCl$_3$) δ (ppm)=31.4 (q, 3C), 34.7 (s), 53.3 (q, 2C), 53.4 (q, 2C), 101.5 (d), 101.8 (d), 123.7 (d), 125.0 (d), 126.8 (d), 133.3 (s), 135.6 (s), 151.2 (s).

EXAMPLE 2

Electrosynthesis of 4-tert-amyl-1,2-bis(dimethoxymethyl)benzene 4-tert-Amyl-1,2-dimethylbenzene is oxidized in the electrolysis cell described in Example 1 under the conditions given therein.

Electrolyte:

1135 g (6.449 mol) of 4-tert-amyl-1,2-dimethylbenzene, 30 g of sodium benzenesulfonate and 2520 g of methanol.

Electrolysis temperature: 31°–33° C.

Electrolysis with 16 F/mol of 4-tert-amyl-1,2-dimethylbenzene.

The electrolyte is worked up as described in Example 1. After purification by distillation under reduced pressure, 1002 g (3.385 mol) of 4-tert-amyl-1,2-bis(dimethoxymethyl)benzene are obtained.

Yield: 53%

$^{13}$C-NMR (CDCl$_3$) δ (ppm)=9.1 (q), 28.5 (q, 2C), 36.9 (t), 38.0 (s), 53.4 (q, 4C), 101.6 (d), 101.8 (d), 124.5 (d), 125.8 (d), 126.7 (d), 133.3 (s), 135.5 (s), 149.6 (s).

We claim:

1. A process for preparing phthalaldehyde tetraalkyl acetals of the formula I

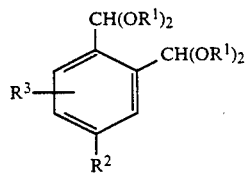

wherein
R$^1$ is C$_1$–C$_6$-alkyl,
R$_2$ is selected from the group consisting of C$_4$–C$_{20}$-alkyl and C$_4$–C$_{20}$-alkyl-cycloalkyl, said groups bearing alkyl substituents on the α-C atom, and
R$^3$ is selected from the group consisting of C$_4$–C$_{20}$-alkyl and C$_4$–C$_{20}$-alkyl-cycloalkyl, said groups bearing alkyl substituents on the α-C atom, or R$^3$ is hydrogen, which comprises electrochemically oxidizing substituted xylenes of the formula II

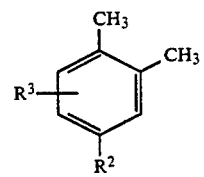

where R$^2$ and R$^3$ have the meanings specified above, in an alcohol R$^4$OH where R$^4$ is C$_1$–C$_8$-alkyl.

2. A process as claimed in claim 1, wherein the electrochemical oxidation are carried out in undivided cells.

3. A process as claimed in claim 1, wherein the electrochemical oxidation are carried out at graphite anodes.

4. A process as claimed in claim 1, wherein the electrochemical oxidation are carried out at 0°–100° C. under atmospheric pressure or superatmospheric pressure.

5. A process as claimed in claim 1, wherein the electrochemical oxidation are carried out with current densities of 0.1–25 A/dm$^2$.

6. The process of claim 1, wherein R$^2$ is selected from the group consisting of C$_4$–C$_{12}$-alkyl and C$_6$–C$_{12}$-alkyl-cycloalkyl, said groups bearing alkyl substituents on the α-C atom.

7. The process of claim 1, wherein R$^3$ is selected from the group consisting of C$_4$–C$_{12}$-alkyl and C$_6$–C$_{12}$-alkyl-cycloalkyl, said groups bearing alkyl substituents on the α-C atom.

* * * * *